United States Patent
Kondo et al.

(10) Patent No.: US 10,286,124 B2
(45) Date of Patent: May 14, 2019

(54) INHALATION DEVICE

(71) Applicant: MURATA MANUFACTURING CO., LTD., Kyoto (JP)

(72) Inventors: Daisuke Kondo, Kyoto (JP); Kenjiro Okaguchi, Kyoto (JP); Hiroshi Takemura, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 319 days.

(21) Appl. No.: 15/383,496

(22) Filed: Dec. 19, 2016

(65) Prior Publication Data
US 2017/0095599 A1 Apr. 6, 2017

Related U.S. Application Data

(63) Continuation of application No. PCT/JP2015/068282, filed on Jun. 25, 2015.

(30) Foreign Application Priority Data

Jul. 2, 2014 (JP) .................................. 2014-136711

(51) Int. Cl.
*A61M 5/00* (2006.01)
*A61M 1/00* (2006.01)

(52) U.S. Cl.
CPC ........ *A61M 1/0066* (2013.01); *A61M 1/0003* (2013.01); *A61M 1/0023* (2013.01);
(Continued)

(58) Field of Classification Search
CPC .............. A61M 1/0066; A61M 1/0072; A61M 1/0003; A61M 1/0023; A61M 1/0052;
(Continued)

(56) References Cited

U.S. PATENT DOCUMENTS 6,821,484 B1   11/2004 Gregersen
2001/0042794 A1   11/2001 Tomkins
(Continued)

FOREIGN PATENT DOCUMENTS

JP    S49-106196 U    9/1974
JP    2002-524134 A    8/2002
(Continued)

OTHER PUBLICATIONS

International Search Report issued in Application No. PCT/JP2015/068282 dated Jul. 21, 2015.
(Continued)

*Primary Examiner* — Amber R Stiles
(74) *Attorney, Agent, or Firm* — Pearne & Gordon LLP

(57) ABSTRACT

An inhalation device includes a nozzle, a separator, a housing, a battery portion, a circuit board, and a piezoelectric blower. The piezoelectric blower has a suction hole that opens near the center of an upper surface of the piezoelectric blower and a discharge hole that opens at the center of a bottom surface of the piezoelectric blower. The piezoelectric blower is mounted on a first main surface of the circuit board on the side of an upper housing. The circuit board applies a drive voltage to the piezoelectric blower to drive the piezoelectric blower. The circuit board has a through-hole facing the discharge hole. The through-hole overlaps the discharge hole, out of the suction hole and the discharge hole, when the first main surface of the circuit board is viewed from a front side.

10 Claims, 14 Drawing Sheets

(52) U.S. Cl.
CPC ......... *A61M 1/0072* (2014.02); *A61M 1/0052* (2014.02); *A61M 2205/42* (2013.01); *A61M 2205/75* (2013.01); *A61M 2205/82* (2013.01)

(58) Field of Classification Search
CPC .......... A61M 2205/42; A61M 2205/75; A61M 2205/82
See application file for complete search history.

(56) References Cited

U.S. PATENT DOCUMENTS

| | | | |
|---|---|---|---|
| 2007/0247009 A1* | 10/2007 | Hoffman | F04D 25/0606 310/51 |
| 2008/0154183 A1 | 6/2008 | Baker | |
| 2010/0324510 A1 | 12/2010 | Andresen | |
| 2015/0050877 A1 | 2/2015 | Yano | |

FOREIGN PATENT DOCUMENTS

| | | |
|---|---|---|
| JP | 2002-538001 A | 11/2002 |
| JP | 2010-527636 A | 8/2010 |
| JP | 5166527 B2 | 3/2013 |
| JP | 2013-229281 A | 11/2013 |
| WO | 2013/187270 A1 | 12/2013 |

OTHER PUBLICATIONS

Written Opinion issued in Application No. PCT/JP2015/068282 dated Jul. 21, 2015.

\* cited by examiner

THICKNESS DIRECTION

LONGITUDINAL DIRECTION

WIDTH DIRECTION

THICKNESS DIRECTION

⊗ ⟶ LONGITUDINAL DIRECTION
WIDTH DIRECTION

THICKNESS DIRECTION

⊗ → LONGITUDINAL DIRECTION
WIDTH DIRECTION

THICKNESS DIRECTION

⊗ → LONGITUDINAL DIRECTION
WIDTH DIRECTION

INHALATION DEVICE

This is a continuation of International Application No. PCT/JP2015/068282 filed on Jun. 25, 2015 which claims priority from Japanese Patent Application No. 2014-136711 filed on Jul. 2, 2014. The contents of these applications are incorporated herein by reference in their entireties.

BACKGROUND OF THE DISCLOSURE

Field of the Disclosure

The present disclosure relates to an inhalation device used to remove, for example, a fluid such as nasal mucus.

Description of the Related Art

Nasal congestion due to excessive secretion of nasal mucus is a symptom of the common cold, rhinitis, and empyema. In general, blowing the nose can settle the nasal congestion. However, in the case of a person who cannot blow his or her nose by oneself, such as an infant, it is necessary for a carer to remove the nasal mucus.

At this time, the use of tissue paper or a swab enables a small amount of nasal mucus to be removed, but it is difficult to remove a large amount of nasal mucus. In view of this, in recent years, inhalation devices that can remove a large amount of nasal mucus by using an electric motor and a pump have been widely used (See, for example, Patent Document 1).

Patent Document 1: Japanese Unexamined Patent Application Publication (Translation of PCT Application) No. 2010-527636

BRIEF SUMMARY OF THE DISCLOSURE

Conventional inhalation devices, however, make a loud motor noise and strongly vibrate when used. In some cases, infants move their bodies in response to the motor noise or the vibration, and this makes it difficult to suck their nasal mucus. In response to this, the applicant has developed an inhalation device that uses a piezoelectric element, which makes only a small motor noise and slightly vibrates when used, instead of an electric motor.

FIG. 17 is a schematic view of an inhalation device 901 that uses a piezoelectric element as a driving source. The inhalation device 901 includes a nozzle 2, a separator 3, and a housing 904. The inhalation device 901 also includes a battery 61, a battery case 62, a circuit board 907, a piezoelectric blower 8, and a stationary portion 10 in the housing 904.

A columnar cavity 11 is formed in the stationary portion 10. The piezoelectric blower 8 is placed on the stationary portion 10.

The circuit board 907 is connected to the battery 61 with a power line L1 interposed therebetween. The circuit board 907 is connected to the piezoelectric blower 8 with a power-supply line L2 interposed therebetween. Electronic components 85 are mounted on the circuit board 907. The circuit board 907 generates a drive voltage from the power supply voltage of the battery 61. The circuit board 907 applies the drive voltage to the piezoelectric blower 8 to drive the piezoelectric blower 8.

The nozzle 2 has an inhalation cavity 90. The nozzle 2 is inserted into, for example, a nasal cavity, and an external fluid is sucked from the inhalation cavity 90. The separator 3 is connected to the rear end of the nozzle 2. The inside of the separator 3 is in communication with the inhalation cavity 90 with the inside of the nozzle 2 interposed therebetween. The separator 3 isolates nasal mucus sucked through the nozzle 2 from air. The housing 904 forms a channel 95 and a channel 96 that are in communication with the inside of the separator 3. An exhaust cavity 47 for a gas is formed in the housing 904.

The piezoelectric blower 8 is connected to the rear end of the separator 3. The piezoelectric blower 8 includes a suction hole 89 for a gas, a discharge hole 99 for the gas, a piezoelectric element, and a vibration plate. The piezoelectric element is attached to the vibration plate. The piezoelectric element, when driven, causes the vibration plate to start a flexural vibration. Consequently, the piezoelectric blower 8 sucks air in the channel 96 isolated by the separator 3 from the suction hole 89 and discharges the air from the discharge hole 99. The air discharged from the discharge hole 99 is exhausted from the exhaust cavity 47 to the outside of the housing 904.

In the inhalation device 901 thus formed, driving of the piezoelectric element is not accompanied by sliding nor friction, and driving noise and vibration can be strongly suppressed.

With the structure of the inhalation device 901, however, the nozzle 2, the separator 3, the piezoelectric blower 8, the circuit board 907, and the battery 61 are aligned in the longitudinal direction. Accordingly, the inhalation device 901 has a problem of being long in the longitudinal direction, although inhalation devices have recently been required to have a smaller body size.

In view of this, an object of the present disclosure is to provide an inhalation device that can have a smaller body size.

An inhalation device according to the present disclosure includes a piezoelectric blower having a suction hole for a gas, a discharge hole for the gas, and a piezoelectric element serving as a driving source, and a circuit board that has a through-hole facing the suction hole or the discharge hole and applies a drive voltage to the piezoelectric element to drive the piezoelectric blower.

The through-hole overlaps the suction hole or the discharge hole that the through-hole faces when a main surface of the circuit board is viewed from a front side.

With this structure, when the drive voltage is applied from the circuit board to the piezoelectric element, the piezoelectric element expands and contracts. The piezoelectric blower is driven by the stretching force of the piezoelectric element. Consequently, the piezoelectric blower sucks the gas from the suction hole via the through-hole of the circuit board and discharges the gas from the discharge hole, or the piezoelectric blower sucks the gas from the suction hole and discharges the gas from the discharge hole via the through-hole of the circuit board.

The inhalation device having the above structure causes the gas to be sucked into the piezoelectric blower, or the gas discharged from the piezoelectric blower to pass through the through-hole of the circuit board. Accordingly, in the inhalation device having the above structure, the piezoelectric blower can be disposed near the circuit board or on the circuit board.

That is, in the inhalation device having the above structure, the circuit board and the piezoelectric blower can be disposed so as to overlap. Accordingly, it is not necessary for the circuit board and the piezoelectric blower to be arranged side by side unlike the inhalation device 901 illustrated in FIG. 17.

Accordingly, the inhalation device having the above structure can have a smaller body size.

In addition, the circuit board, the battery, or another component can be cooled in a manner in which the circuit board, the battery, or the other component is exposed to the gas discharged from the discharge hole via the through-hole of the circuit board.

The piezoelectric blower is preferably mounted on the main surface of the circuit board.

With this structure, mounting the piezoelectric blower directly on the circuit board compensates a decrease in strength due to the through-hole formed in the circuit board and enables an improvement in the strength.

A power-supply pattern for supplying the drive voltage is preferably formed on the main surface of the circuit board. The piezoelectric blower preferably includes an electrode terminal joined to the power-supply pattern.

With this structure, a power-supply line connecting the piezoelectric blower to the circuit board can be omitted. This enables simplification of the structure, space reduction, and cost reduction to be achieved.

The through-hole is preferably wider than the suction hole or the discharge hole that the through-hole faces and contains the suction hole or the discharge hole that the through-hole faces when the main surface of the circuit board is viewed from the front side.

With this structure, the whole gas discharged from the piezoelectric blower passes through the through-hole. That is, the gas discharged from the piezoelectric blower is not impeded by the circuit board.

Accordingly, this structure enables a decrease in the suction force of the piezoelectric blower to be prevented.

The inhalation device preferably includes a housing accommodating the piezoelectric blower and the circuit board. The housing preferably has a first cavity exposed to an outside of the housing and in communication with the suction hole with a first channel interposed therebetween and a second cavity exposed to the outside of the housing and in communication with the discharge hole with a second channel interposed therebetween.

The housing is preferably formed of a first housing having the first cavity and a second housing having the second cavity.

The inhalation device according to the present disclosure can have a smaller body size.

DETAILED DESCRIPTION OF THE DISCLOSURE

An inhalation device according to a first embodiment of the present disclosure will hereinafter be described with reference to the drawings.

Figure 1:
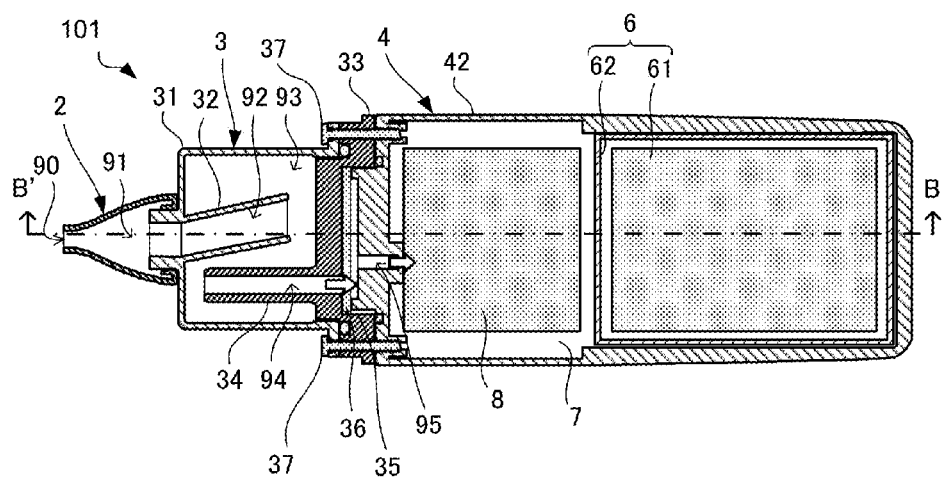
FIG. 1 is a sectional plan view of an inhalation device 101 according to a first embodiment of the present disclosure.
Figure 1:
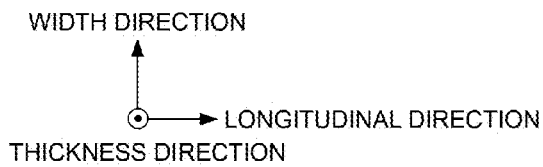
Figure 2:
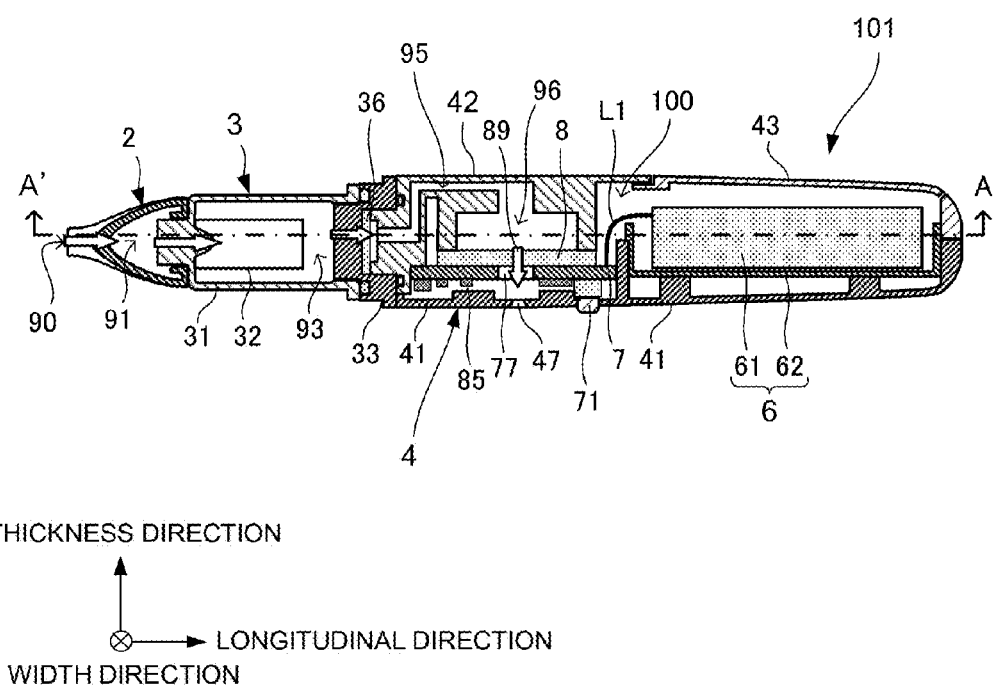
FIG. 2 is a sectional side view of the inhalation device 101 according to the first embodiment of the present disclosure.
Figure 3:
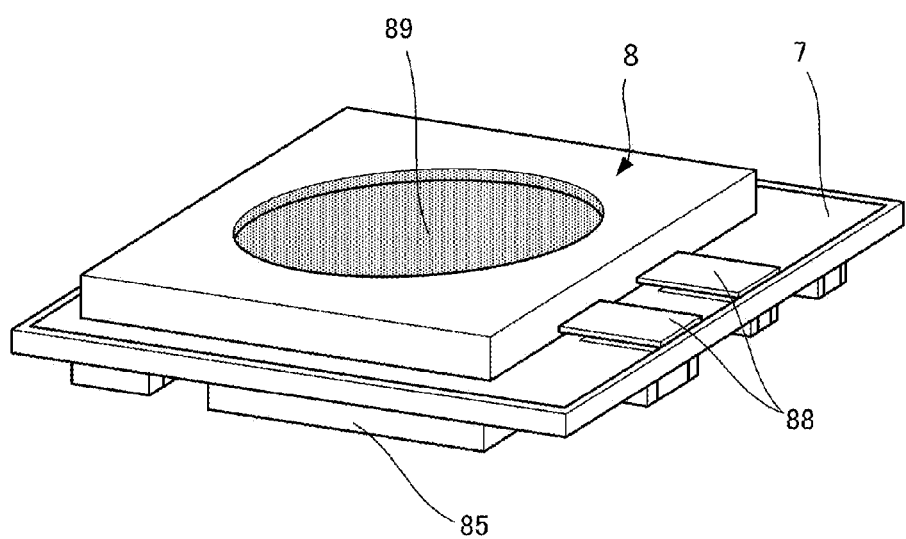
FIG. 3 is an external perspective view of a piezoelectric blower 8 and a circuit board 7 illustrated in FIG. 2.
Figure 4:
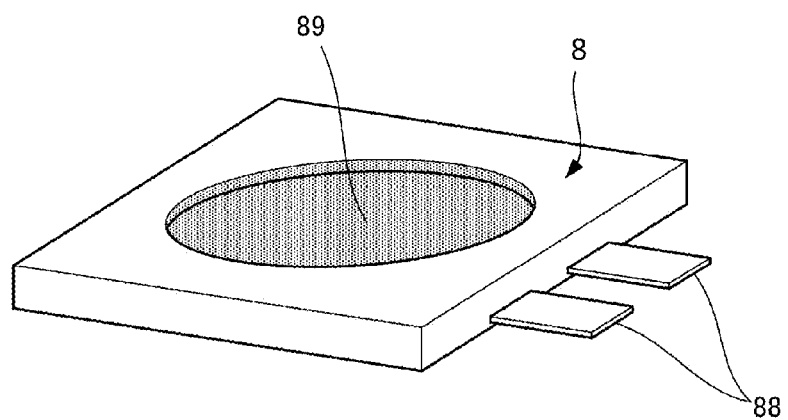
FIG. 4 is an exploded perspective view of the piezoelectric blower 8 and the circuit board 7 illustrated in FIG. 2.
Figure 4:
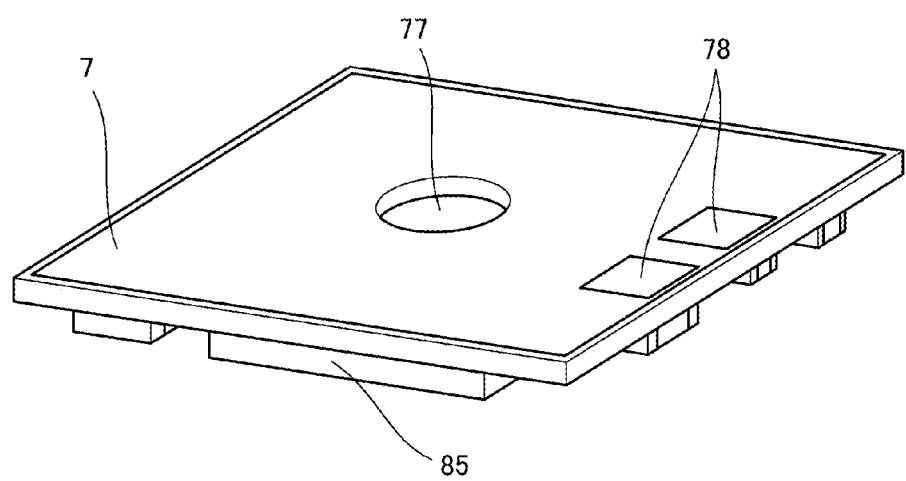

FIG. 1 is a sectional plan view of an inhalation device 101 according to the first embodiment viewed from the upper surface side. FIG. 2 is a sectional side view of the inhalation device 101 according to the first embodiment viewed from the side surface side. FIG. 3 is an external perspective view of a piezoelectric blower 8 and a circuit board 7 illustrated in FIG. 2. FIG. 4 is an exploded perspective view of the piezoelectric blower 8 and the circuit board 7 illustrated in FIG. 2.

FIG. 1 illustrates a section located at the position illustrated by a one-dot chain line A-A' in FIG. 2. Arrows in FIG. 1 represent the flow of a gas. FIG. 2 illustrates a section located at the position illustrated by a one-dot chain line B-B' in FIG. 1. Arrows in FIG. 2 represent the flow of the gas.

The inhalation device 101 illustrated in FIG. 1 and FIG. 2 is an inhalation device for a liquid such as nasal mucus. The inhalation device 101 has an overall elongated shape that extends in a longitudinal direction and is used with a side thereof in the longitudinal direction (referred to as a front side) facing, for example, a patient. The inhalation device 101 is formed so as to extend in a width direction and a thickness direction that are perpendicular to the longitudinal direction and is formed to be thin such that the dimension in the thickness direction is less than the dimension in the width direction.

A schematic structure of the inhalation device 101 is as follows. The inhalation device 101 includes a nozzle 2, a separator 3, and a housing 4. The nozzle 2, the separator 3, and the housing 4 are aligned in this order from the front side to the rear side in the longitudinal direction.

The nozzle 2 is inserted into the nasal cavity of, for example, a patient when the inhalation device 101 is used, and a fluid such as nasal mucus is sucked therefrom. The separator 3 isolates and stores a mixture such as nasal mucus contained in the fluid sucked through the nozzle 2 when the inhalation device 101 is used. A gas (air in the embodiment) after the mixture is isolated from the fluid is sucked from the separator 3 into the inside of the housing 4. The housing 4 is held by, for example, an operator during use.

The inhalation device 101 includes a battery portion 6, the circuit board 7, and the piezoelectric blower 8 as built-in components of the housing 4. The battery portion 6 includes a battery 61 and a battery case 62. The battery case 62 holds the battery 61 in a replaceable manner.

The circuit board 7 forms a power-supply circuit and includes a power switch 71. The power switch 71 is exposed from an opening formed in the housing 4 to the outside. The circuit board 7 switches on or off the power supply from the battery portion 6 to the piezoelectric blower 8 in accordance with a pressed state of the power switch 71.

The piezoelectric blower 8 applies a negative pressure to channels in the housing 4 and sucks the gas from the separator 3 into the inside of the housing 4.

The detailed structure of components will now be described.

The nozzle 2 is formed of an elastic material body. The external shape of the nozzle 2 is inclined so as to taper toward the front side. An inhalation cavity 90 and a channel 91 are formed in the nozzle 2. The inhalation cavity 90 is a cavity that is formed at the front end of the nozzle 2 and through which an external fluid containing, for example, nasal mucus is inhaled.

The channel 91 is formed so as to extend through the inside of the nozzle 2 in the longitudinal direction and is in communication with the inhalation cavity 90. The nozzle 2 is connected to the front side of the separator 3 in an airtight state and can be detached from the separator 3.

The separator 3 includes a case 31, a tubular portion 32, a cap 33, and a tubular portion 34. The case 31 is a member having a box shape and having an opening at the rear side. The tubular portion 32 is a tubular member attached to the case 31, extends from the front surface of the case 31 toward the front side, and extends from the inner bottom surface around the opening of the case 31 toward the rear side.

The nozzle 2 is fitted to the front end of the tubular portion 32. The cap 33 is a lid-like member fitted to a rear-side portion of the case 31. The tubular portion 34 is a tubular member attached to the cap 33 and extends from the cap 33 toward the front side.

Channels 92, 93, and 94 are formed in the separator 3. The channel 92 is formed so as to extend through the inside of the tubular portion 32 in the longitudinal direction and is in communication with the channel 91 of the nozzle 2. The channel 93 is formed inside the case 31 and is in communication with the channel 92 in the tubular portion 32. The channel 94 is formed so as to extend through the inside of the tubular portion 34 in the longitudinal direction and is in communication with the channel 93 of the case 31.

The tubular portion 32 and the tubular portion 34 are arranged so as to alternate in the longitudinal direction inside the case 31, and the channel 92 and the channel 94 are in communication with each other with the channel 93 interposed therebetween. Thus, it is difficult for the liquid, such as nasal mucus, contained in the fluid introduced from the nozzle 2 into the separator 3 to leak from the inside (channel 93) of the case 31, and only the gas contained in the fluid is sucked from the separator 3 into the inside of the housing 4.

A recessed portion 35 is formed on the rear surface of the cap 33. The separator 3 is connected to the front side of the housing 4 in an airtight state in a manner in which the housing 4 is fitted into the recessed portion 35. A filter 36 is disposed on the inner bottom surface of the recessed portion 35.

The filter 36 is a non-woven paper membrane or a spongiform membrane and has a function of preventing the liquid, such as nasal mucus, from leaking from the side of the separator 3 to the side of the housing 4. The filter 36 is not necessarily disposed thereon.

The separator 3 is connected to the housing 4 with a screw 37 and can be isolated from the housing 4 by unscrewing the screw 37. Also, the case 31 and the cap 33 can be separated from each other by unscrewing the screw 37.

This enables removal of the nasal mucus from the separator 3 and cleaning. O-rings are appropriately disposed at the joints of the components for airtightness. The components may be connected so as to be isolable with another connector other than the screw 37 or may be formed integrally with each other.

The housing 4 is formed of a lower housing 41, an upper housing 42, and a battery cover 43. The lower housing 41 has a thin box shape having an opening on the upper surface side in the thickness direction. The upper housing 42 has a thin box shape having an opening on the bottom surface side in the thickness direction.

The upper housing 42 is connected to the lower housing 41 so as to form a container shape. Thus, the lower housing 41, the battery cover 43, and a part of the upper housing 42 form an interior space 100. In the interior space 100, the battery portion 6, the circuit board 7, and the piezoelectric blower 8 are accommodated.

The opening formed in the lower housing 41 on the upper surface side enables the battery 61 of the battery portion 6 to be replaced. The battery cover 43 is attached to the upper surface side of the lower housing 41 so as to cover the opening. The exhaust cavity 47, described in detail later, is formed in the lower housing 41. The interior space 100 is in communication with a space outside the housing 4 with a joint portion between the upper housing 42 and the battery cover 43 and the exhaust cavity 47 interposed therebetween and has the same pressure as the outside pressure.

The lower housing 41 and the upper housing 42 hold the circuit board 7 in the interior space 100.

The channel 95 and the channel 96 are formed inside the upper housing 42. The channel 95 is in communication with the channel 94 of the separator 3. The channel 95 extends inside the upper housing 42 from a junction with the channel 94 toward the rear side in the longitudinal direction, is bent into an inverted U-shape midway therebetween, and is in communication with the channel 96. The channel 96 is columnar and in communication with the suction hole 89 of the piezoelectric blower 8.

The piezoelectric blower 8 has a plate shape and is joined to the upper housing 42 so as to make the channel 95 and the channel 96 airtight. The piezoelectric blower 8 includes the suction hole 89 that opens near the center of the upper surface of the piezoelectric blower 8 and a discharge hole 99 that opens at the center of the bottom surface of the piezoelectric blower 8. The piezoelectric blower 8 is mounted on a first main surface (one main surface) of the circuit board 7 on the side of the upper housing 42.

Examples of a method of joining the piezoelectric blower 8 and the circuit board 7 include adhesion with an adhesive, fixation with a double-side tape, fastening with a screw, fitting to a protrusion formed on a driving circuit, spot welding, and fitting into a dug portion.

The circuit board 7 is connected to the battery 61 with the power line L1 interposed therebetween. Power-supply patterns 78 are formed on the first main surface of the circuit board 7. Electronic components 85 are mounted on a second main surface (the other main surface) of the circuit board 7 on the side of the lower housing 41. The circuit board 7 generates a drive voltage from the power supply voltage of the battery 61. The circuit board 7 applies the drive voltage to the piezoelectric blower 8 to drive the piezoelectric blower 8.

The circuit board 7 has a through-hole 77 facing the discharge hole 99. The through-hole 77 overlaps the discharge hole 99, out of the suction hole 89 and the discharge hole 99, when the first main surface of the circuit board 7 is viewed from the front side. The through-hole 77 is wider than the discharge hole 99 and contains the discharge hole 99 when the first main surface of the circuit board 7 is viewed from the front side.

In the inhalation device 101, when the power switch 71 is turned on, and the piezoelectric blower 8 is driven, the piezoelectric blower 8 sucks the gas from the channel 96 via the suction hole 89 and discharges the gas from the discharge hole 99 into the interior space 100 via the through-hole 77. The gas discharged from the discharge hole 99 is exhausted from the exhaust cavity 47. Consequently, a negative pressure is applied to the channel 96.

Accordingly, in the inhalation device 101 as a whole, the negative pressure applied to the channel 96 in the housing 4 causes the flow of the fluid through the channel 95 of the housing 4, the channels 94, 93, and 92 of the separator 3, and the channel 91 of the nozzle 2, and an external fluid is sucked from the inhalation cavity 90 of the nozzle 2.

The inhalation cavity 90 corresponds to the first cavity according to the present disclosure. The exhaust cavity 47 corresponds to the second cavity according to the present disclosure. The channel 96, the channel 95, the channel 94, the channel 93, the channel 92, and the channel 91 correspond to the first channel according to the present disclosure. The interior space 100 corresponds to the second channel according to the present disclosure. The nozzle 2, the separator 3, and a part of the upper housing 42 forming the channel 96 and the channel 95 correspond to the first housing according to the present disclosure. The lower housing 41, the battery cover 43, and a part of the upper housing 42 forming the interior space 100 correspond to the second housing according to the present disclosure.

The detailed structure of the piezoelectric blower 8 will now be described.

Figure 5:
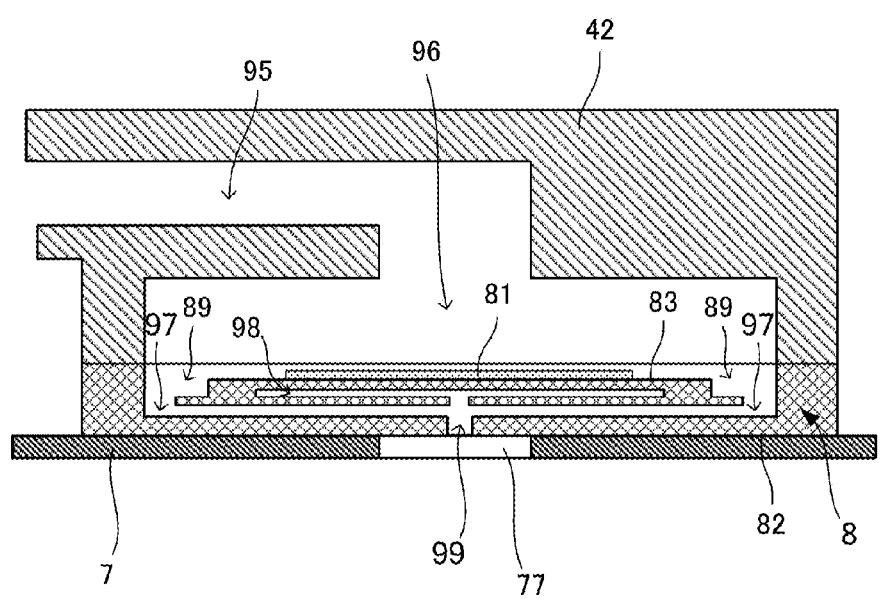
FIG. 5 is an enlarged sectional view of the piezoelectric blower 8 illustrated in FIG. 2.
Figure 5:
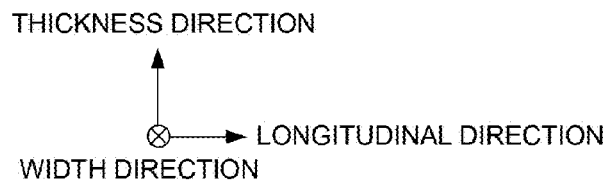

FIG. 5 is an enlarged sectional side view of the vicinity of the piezoelectric blower 8. The piezoelectric blower 8 includes a piezoelectric element 81, a structural body 82, and electrode terminals 88. The structural body 82 is discoid. The suction hole 89 opens near the center of the upper surface of the structural body 82. The discharge hole 99 opens at the center of the bottom surface of the structural body 82. A channel 97 and a pump chamber 98 are formed inside the structural body 82.

The channel 97 is in communication with the suction hole 89 and the discharge hole 99. The pump chamber 98 is a narrow columnar space and in communication with a part of the channel 97 that faces the discharge hole 99. The pump chamber 98 forms some of the channels in the inhalation device 101 together with the channel 97.

The structural body 82 is composed of, for example, stainless steel (SUS). The ceiling of the pump chamber 98 in the structural body 82 is formed as a vibration plate 83 that enables a flexural vibration. The vibration plate 83 is discoid, the bottom surface thereof faces the pump chamber 98, and the piezoelectric element 81 is attached to the upper surface thereof. The bottom surface of the vibration plate 83 faces the discharge hole 99 with the pump chamber 98 interposed therebetween.

The piezoelectric element 81 is composed of, for example, PZT ceramics. The piezoelectric element 81 has a discoid shape that is thin in the thickness direction and has piezoelectricity such that, when an alternating drive voltage is applied from the circuit board 7 thereto, the piezoelectric element 81 tries to expand and contract in a plane direction.

Electrodes are disposed on both main surfaces of the piezoelectric element 81. The electrodes on both main surfaces of the piezoelectric element 81 are connected to the electrode terminals 88. The electrode terminals 88 are joined to the power-supply patterns 78 of the circuit board 7.

Figure 6A:
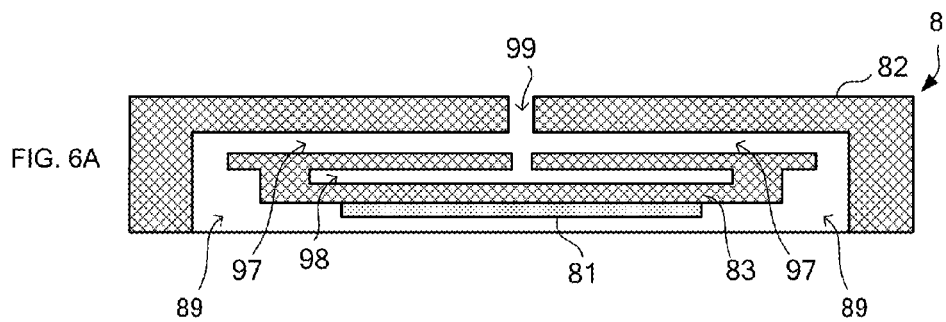
FIGS. 6A, 6B and 6C Each of FIGS. 6A, 6B and 6C is a schematic view of the piezoelectric blower 8 illustrated in FIG. 2 illustrating the vibration mode thereof.
Figure 6B:
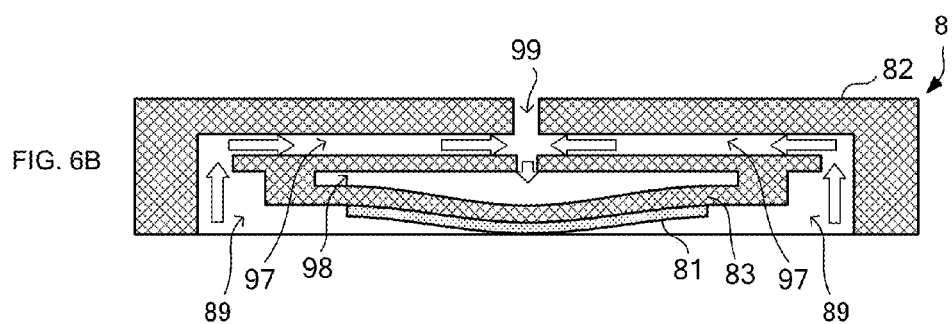
Figure 6C:
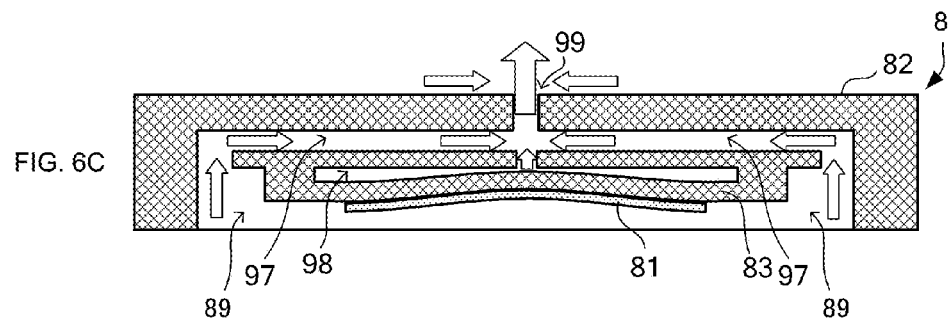

The vibration mode of the piezoelectric blower 8 will now be described. Each of FIGS. 6A, 6B and 6C is a schematic view of the piezoelectric blower 8 illustrating the vibration mode thereof. Arrows in each of FIGS. 6B and 6C represent the flow of a gas.

The piezoelectric element 81 and the vibration plate 83 are attached to each other to form a unimorph structure. When an alternating drive voltage is applied from the circuit board 7 to the electrodes of the piezoelectric element 81 via the electrode terminals 88, the piezoelectric element 81 expands and contracts. The expansion and contraction of the piezoelectric element 81 causes the piezoelectric element 81 and the vibration plate 83 to periodically repeat flexural vibrations concentrically as illustrated in FIG. 6B and FIG. 6C.

Specifically, in the case where the piezoelectric element 81 starts to expand from a rest state illustrated in FIG. 6A, as illustrated in FIG. 6B, the vibration plate 83 bends toward the side of the piezoelectric element 81 (bottom surface side) into a convex shape, and the volume of the pump chamber 98 increases. Consequently, a negative pressure is applied to the pump chamber 98. The negative pressure is also applied to the channel 97 in communication with the pump chamber 98, and the fluid in the channel 97 is sucked into the pump chamber 98.

In the case where the piezoelectric element 81 starts to contract, as illustrated in FIG. 6C, the vibration plate 83 bends toward the side of the pump chamber 98 (upper surface side) into a convex shape, and the volume of the pump chamber 98 decreases. Consequently, the gas in the pump chamber 98 is discharged from the discharge hole 99 to the outside (interior space 100) via the through-hole 77, and the flow of the gas draws the gas in the channel 97 and causes the gas in the channel 97 to be discharged from the discharge hole 99 to the outside (interior space 100) via the through-hole 77. The gas discharged into the interior space 100 is exhausted from the exhaust cavity 47 to the outside of the housing 4 (see FIG. 2).

Thus, in the piezoelectric blower 8, the flexural vibrations of the piezoelectric element 81 and the vibration plate 83 are accompanied by repetitive, periodic variations in volume and in pressure of the pump chamber 98, and inertia force acts on the flow of the gas. This steadily keeps the gas flow that causes the fluid in the channel 97 to be discharged from the discharge hole 99.

In the piezoelectric blower 8, no members rub together (slide), and accordingly, driving noise and vibration that are created are slighter than in the case of a conventional electric motor type of driving part. Accordingly, driving noise and vibration of the piezoelectric blower 8 that leak from the inhalation device 101 to the outer space are extremely slight.

In the inhalation device 101, the gas discharged from the piezoelectric blower 8 passes through the through-hole 77 of the circuit board 7. Accordingly, in the inhalation device 101, the piezoelectric blower 8 can be disposed near the circuit board 7 or on the circuit board 7.

That is, in the inhalation device 101, the circuit board 7 and the piezoelectric blower 8 can be disposed so as to overlap. Accordingly, it is not necessary for the circuit board 907 and the piezoelectric blower 8 to be arranged side by side in the longitudinal direction unlike the inhalation device 901 illustrated in FIG. 17.

Accordingly, the inhalation device 101 can have a smaller body size.

In the inhalation device 101, the piezoelectric blower 8 is mounted directly on the circuit board 7. Accordingly, in the inhalation device 101, a decrease in strength due to the through-hole 77 formed in the circuit board 7 can be compensated, and the strength can be improved.

The piezoelectric blower 8 includes the electrode terminals 88 joined to the power-supply patterns 78.

Accordingly, in the inhalation device 101, the power-supply line L2 (see FIG. 17) connecting the piezoelectric blower 8 to the circuit board 7 can be omitted. This enables simplification of the structure, space reduction, and cost reduction to be achieved.

The through-hole 77 is wider than the hole and contains the hole when the main surface of the circuit board 7 is viewed from the front side.

Accordingly, in the inhalation device 101, the whole gas discharged from the piezoelectric blower 8 passes through the through-hole 77. That is, the gas discharged from the piezoelectric blower 8 is not impeded by the circuit board 7.

Accordingly, in the inhalation device 101, a decrease in the suction force of the piezoelectric blower 8 can be prevented.

An inhalation device according to a second embodiment of the present disclosure will now be described.

Figure 7:
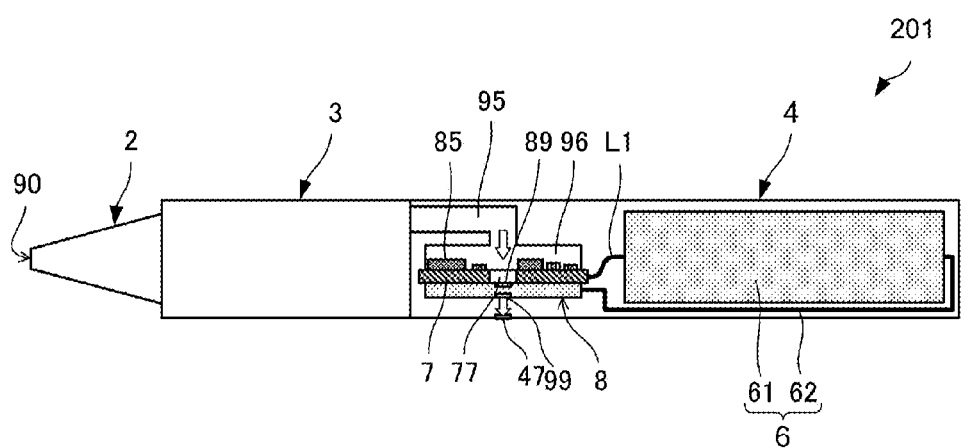
FIG. 7 is a sectional side view of an inhalation device 201 according to a second embodiment of the present disclosure.
Figure 7:
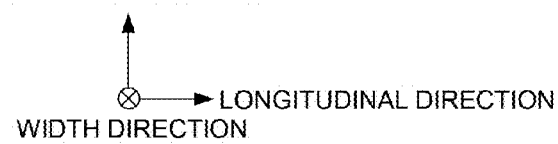
Figure 8:
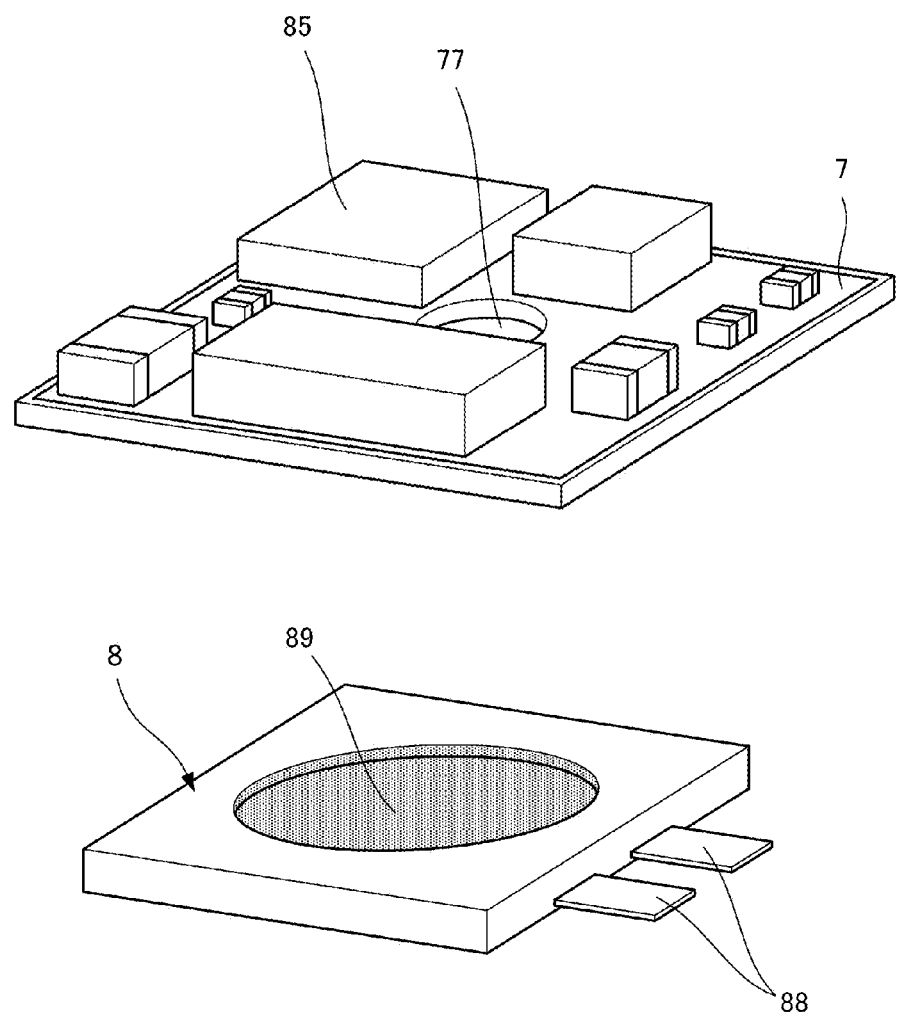
FIG. 8 is an exploded perspective view of the piezoelectric blower 8 and the circuit board 7 illustrated in FIG. 7.

FIG. 7 is a sectional side view of an inhalation device 201 according to the second embodiment of the present disclosure. FIG. 8 is an exploded perspective view of the piezoelectric blower 8 and the circuit board 7 illustrated in FIG. 7.

FIG. 7 is a schematic view in which a detailed illustration is omitted for simplification. Arrows in FIG. 7 represent the flow of a gas.

A difference between the inhalation device 201 according to the second embodiment and the inhalation device 101 is the arrangement of the circuit board 7 and the piezoelectric blower 8. Other features are the same as in the inhalation device 101, and accordingly, the description thereof is omitted.

The piezoelectric blower 8 is mounted on the first main surface (one main surface) of the circuit board 7. The through-hole 77 of the circuit board 7 faces the suction hole 89. The through-hole 77 overlaps the suction hole 89 when the first main surface of the circuit board 7 is viewed from the front side. The electrode terminals 88 of the piezoelectric blower 8 are joined to the power-supply patterns 78 of the circuit board 7.

With this structure, the piezoelectric blower 8 sucks the gas from the suction hole 89 via the through-hole 77 of the circuit board 7 and discharges the gas from the discharge hole 99 when driven.

In the inhalation device 201, the gas to be sucked into the piezoelectric blower 8 passes through the through-hole 77 of the circuit board 7. Accordingly, in the inhalation device 201, the piezoelectric blower 8 can be disposed near the circuit board 7 or on the circuit board 7.

That is, in the inhalation device 201, the circuit board 7 and the piezoelectric blower 8 can be disposed so as to overlap. Accordingly, it is not necessary for the circuit board 7 and the piezoelectric blower 8 to be arranged side by side in the longitudinal direction unlike the inhalation device 901 illustrated in FIG. 17.

Accordingly, the inhalation device 201 can have a smaller body size as in the case of the inhalation device 101.

An inhalation device according to a third embodiment of the present disclosure will now be described.

Figure 9:
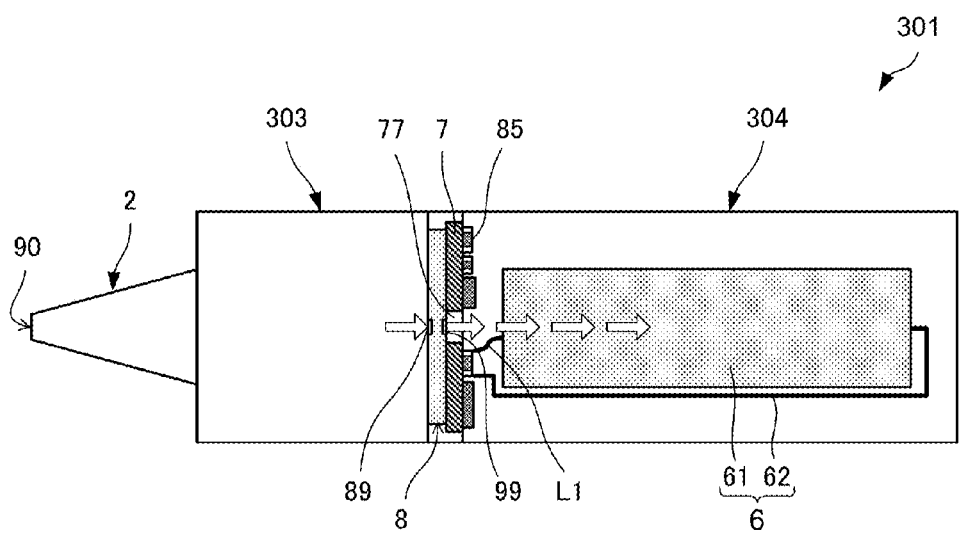
FIG. 9 is a sectional side view of an inhalation device 301 according to a third embodiment of the present disclosure.
Figure 9:
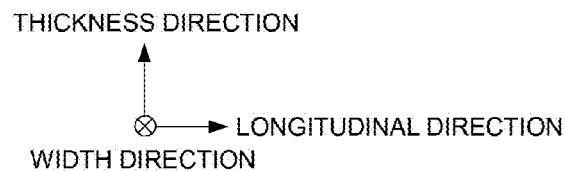

FIG. 9 is a sectional side view of an inhalation device 301 according to the third embodiment of the present disclosure.

FIG. 9 is a schematic view in which a detailed illustration is omitted for simplification. Arrows in FIG. 9 represent the flow of a gas.

A difference between the inhalation device 301 according to the third embodiment and the inhalation device 101 is the arrangement of the circuit board 7 and the piezoelectric blower 8. The inhalation device 301 includes a separator 303 and a housing 304 that are thick in accordance with the arrangement of the circuit board 7 and the piezoelectric blower 8. Other features are the same as in the inhalation device 101, and accordingly, the description thereof is omitted.

Also, in this embodiment, the piezoelectric blower 8 is mounted on the first main surface (one main surface) of the circuit board 7. The through-hole 77 of the circuit board 7 faces the discharge hole 99. The through-hole 77 overlaps the discharge hole 99, out of the suction hole 89 and the discharge hole 99, when the first main surface of the circuit board 7 is viewed from the front side. The through-hole 77 is wider than the discharge hole 99 and contains the discharge hole 99 when the first main surface of the circuit board 7 is viewed from the front side.

In the inhalation device 301, the gas discharged from the piezoelectric blower 8 passes through the through-hole 77 of the circuit board 7. Accordingly, in the inhalation device 301, the piezoelectric blower 8 can be disposed near the circuit board 7 or on the circuit board 7.

That is, in the inhalation device 301, the circuit board 7 and the piezoelectric blower 8 can be disposed so as to overlap. Accordingly, it is not necessary for the circuit board 907 and the piezoelectric blower 8 to be arranged side by side in the longitudinal direction unlike the inhalation device 901 illustrated in FIG. 17.

Accordingly, the inhalation device 301 can have a smaller body size as in the case of the inhalation device 101. The length of the inhalation device 301 in the longitudinal direction can be smaller than the length of the inhalation device 101.

In the inhalation device 301, the circuit board 7 and the piezoelectric blower 8 are arranged such that the discharge hole 99 and the through-hole 77 of the circuit board 7 faces the battery. That is, the circuit board 7 and the piezoelectric blower 8 are arranged such that the battery is exposed to the gas that is discharged from the discharge hole 99 and passes through the through-hole 77 of the circuit board 7. This enables the battery 61 to be cooled in the inhalation device 301.

An inhalation device according to a fourth embodiment of the present disclosure will now be described.

Figure 10:
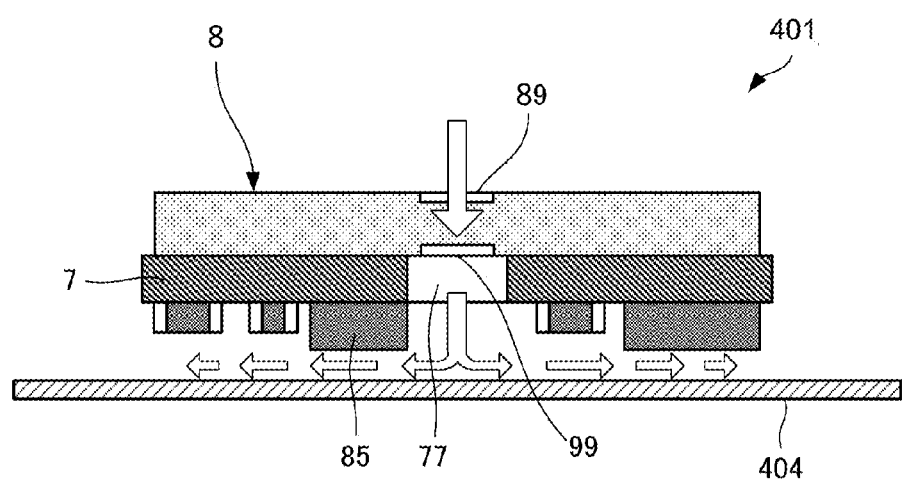
FIG. 10 is a sectional side view of a principal part of an inhalation device 401 according to a fourth embodiment of the present disclosure.

FIG. 10 is a sectional side view of a principal a part of an inhalation device 401 according to the fourth embodiment of the present disclosure.

FIG. 10 is a schematic view in which a detailed illustration is omitted for simplification. Arrows in FIG. 10 represent the flow of a gas.

The inhalation device 401 according to the fourth embodiment differs from the inhalation device 101 in including a housing 404 having no exhaust cavity 47. Other features are the same as in the inhalation device 101, and accordingly, the description thereof is omitted.

In the inhalation device 401, the housing 404 has no exhaust cavity 47. Accordingly, the gas that is discharged from the discharge hole 99 and passes through the through-hole 77 of the circuit board 7 is impeded by the housing 404 and flows in a plane direction of the second main surface of the circuit board 7. This enables the electronic components 85 on the circuit board 7 to be cooled in the inhalation device 401.

An inhalation device according to a fifth embodiment of the present disclosure will now be described.

Figure 11:
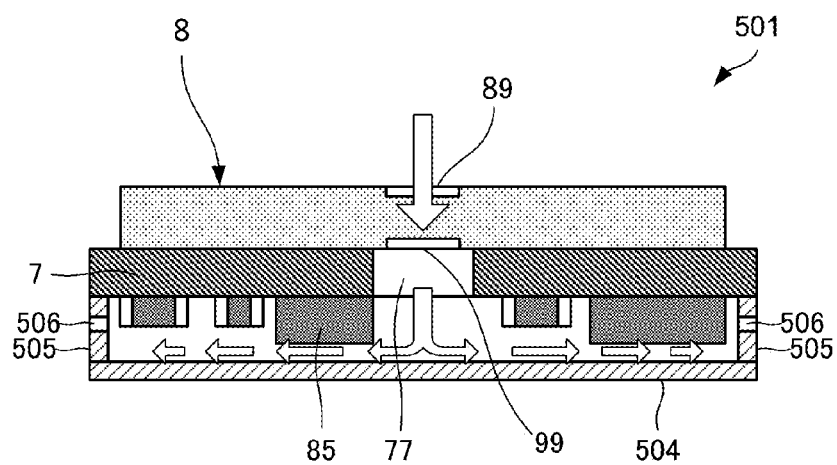
FIG. 11 is a sectional side view of a principal part of an inhalation device 501 according to a fifth embodiment of the present disclosure.

FIG. 11 is a sectional side view of a principal part of an inhalation device 501 according to the fifth embodiment of the present disclosure.

FIG. 11 is a schematic view in which a detailed illustration is omitted for simplification. Arrows in FIG. 11 represent the flow of a gas.

The inhalation device 501 according to the fifth embodiment differs from the inhalation device 101 in including a cover 504. The cover 504 is attached to the circuit board 7 by using a support 505. The support 505 has vents 506. Other features are the same as in the inhalation device 101, and accordingly, the description thereof is omitted.

The inhalation device 501 includes the cover 504. Accordingly, the gas that is discharged from the discharge hole 99 and passes through the through-hole 77 of the circuit board 7 is impeded by the cover 504 and flows in a plane direction of the second main surface of the circuit board 7. This enables the electronic components 85 on the circuit board 7 to be cooled in the inhalation device 501.

An inhalation device according to a sixth embodiment of the present disclosure will now be described.

Figure 12:
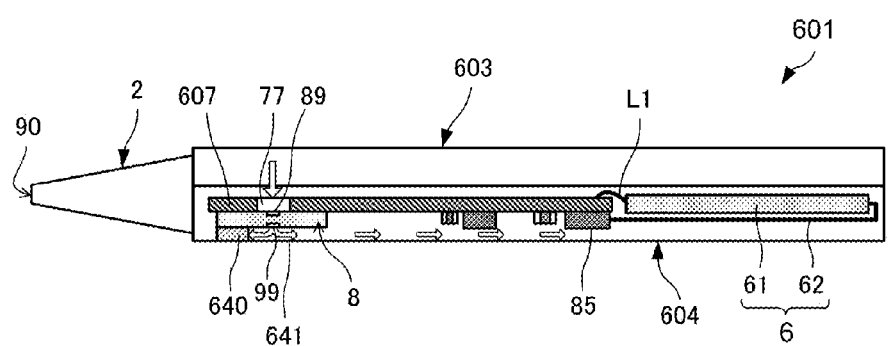
FIG. 12 is a sectional side view of an inhalation device 601 according to a sixth embodiment of the present disclosure.
Figure 13:
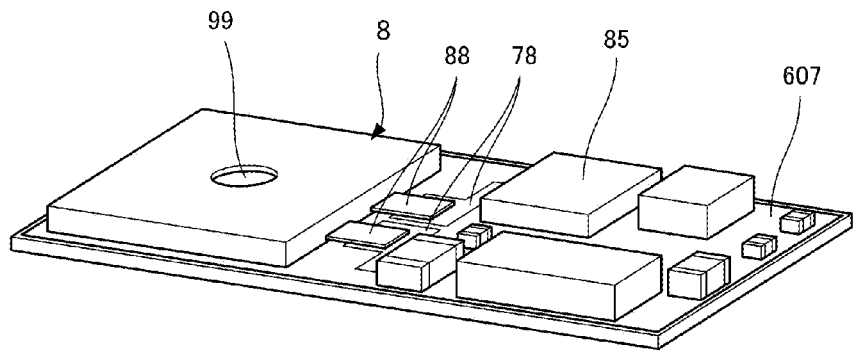
FIG. 13 is an external perspective view of the piezoelectric blower 8 and a circuit board 607 illustrated in FIG. 12.
Figure 14:
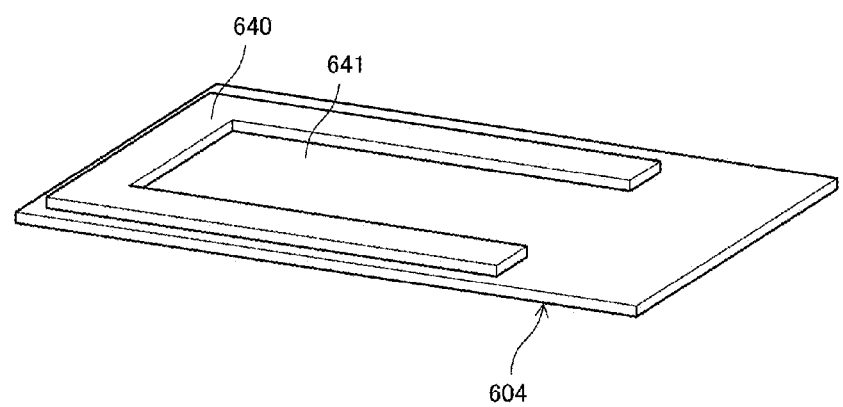
FIG. 14 is an external perspective view of a principal part of a housing 604 illustrated in FIG. 12.

FIG. 12 is a sectional side view of an inhalation device 601 according to the sixth embodiment of the present disclosure. FIG. 13 is an external perspective view of the piezoelectric blower 8 and a circuit board 607 illustrated in FIG. 12. FIG. 14 is an external perspective view of a principal part of a housing 604 illustrated in FIG. 12.

FIG. 12 is a schematic view in which a detailed illustration is omitted for simplification. Arrows in FIG. 12 represent the flow of a gas.

Main differences between the inhalation device 601 according to the sixth embodiment and the inhalation device 101 are the circuit board 607 and the housing 604. The circuit board 607 is longer than the circuit board 7 of the inhalation device 101 in the longitudinal direction. The electronic components 85 and the piezoelectric blower 8 are mounted on the same surface of the circuit board 607.

The housing 604 is elongated in the longitudinal direction in accordance with the length of the circuit board 607 in the longitudinal direction. The housing 604 has no exhaust cavity 47 but has a U-shaped protrusion 640 and a wall 641. The upper surface of the protrusion 640 is joined to the bottom surface of the piezoelectric blower 8. A separator 603 is elongated in the longitudinal direction in accordance with the length of the housing 604 in the longitudinal direction.

The other features of the inhalation device 601 are the same as the inhalation device 101, and accordingly, the description thereof is omitted.

With this structure, the piezoelectric blower 8 sucks the gas from the suction hole 89 via the through-hole 77 and discharges the gas from the discharge hole 99 to the outside when driven.

In the inhalation device 601, the gas to be sucked by the piezoelectric blower 8 passes through the through-hole 77 of the circuit board 607. Accordingly, in the inhalation device 601, the piezoelectric blower 8 can be disposed near the circuit board 607 or on the circuit board 607.

That is, in the inhalation device 601, the circuit board 607 and the piezoelectric blower 8 can be disposed so as to overlap.

Figure 17:
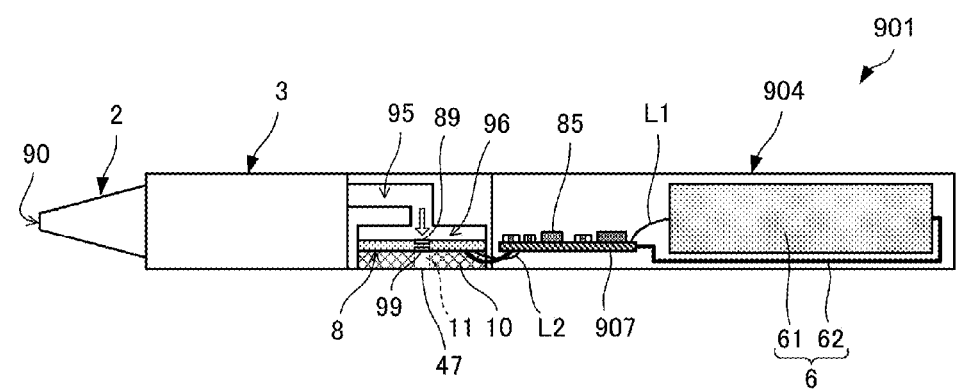
FIG. 17 is a sectional side view of an inhalation device 901 in a comparative example of the present disclosure.

Accordingly, it is not necessary for the circuit board 607 and the piezoelectric blower 8 to be arranged side by side in the longitudinal direction unlike the inhalation device 901 illustrated in FIG. 17.

Accordingly, the inhalation device 601 can have a smaller body size as in the case of the inhalation device 101.

In the inhalation device 601, the housing 604 has no exhaust cavity 47 but has the U-shaped protrusion 640 and the wall 641. Accordingly, the gas discharged from the discharge hole 99 is impeded by the protrusion 640 and the wall 641 and flows toward the side of the electronic components 85 on the circuit board 607.

This enables the electronic components 85 on the circuit board 607 to be cooled in the inhalation device 601.

Since the electronic components 85 and the piezoelectric blower 8 are mounted on the same surface of the circuit board 607, the inhalation device 601 can have a body thickness less than the thickness of the inhalation device 101.

The same effects as in the inhalation device 101 can be achieved also in the case where n piezoelectric blowers are arranged in series or in parallel.

The case where the n piezoelectric blowers are arranged in series will be first described.

Figure 15:
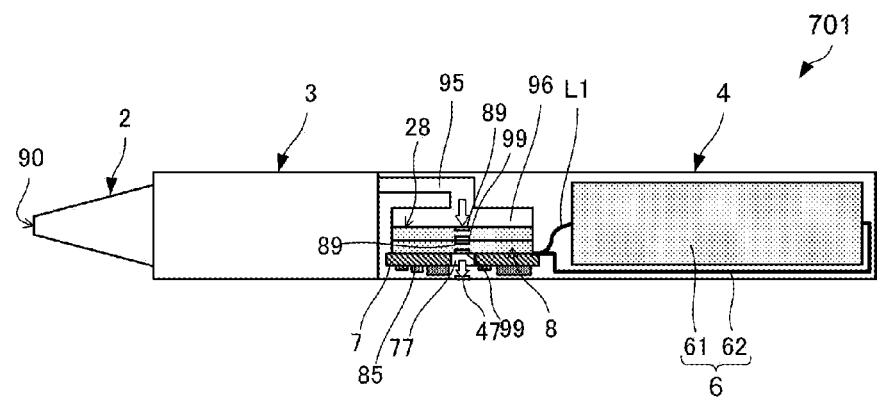
FIG. 15 is a sectional side view of an inhalation device 701 according to a seventh embodiment of the present disclosure.

FIG. 15 is a sectional side view of an inhalation device 701 according to a seventh embodiment of the present disclosure.

FIG. 15 illustrates the case of n=2. FIG. 15 is a schematic view in which a detailed illustration is omitted for simplification. Arrows in FIG. 15 represent the flow of a gas.

The inhalation device 701 according to the seventh embodiment differs from the inhalation device 101 in including a piezoelectric blower 28. Other features are the same as in the inhalation device 101, and accordingly, the description thereof is omitted.

The structure of the piezoelectric blower 28 is the same as the piezoelectric blower 8. The piezoelectric blower 8 and the piezoelectric blower 28 are stacked such that the discharge hole 99 of the piezoelectric blower 28 is in communication with the suction hole 89 of the piezoelectric blower 8. That is, the piezoelectric blower 28 and the piezoelectric blower 8 are arranged in series. The electrode terminals 88 of the piezoelectric blower 28 are connected to the power-supply patterns of the circuit board 7.

The piezoelectric blower 8 is mounted on the first main surface (one main surface) of the circuit board 7 on the side of the upper housing 42. The through-hole 77 of the circuit board 7 faces the discharge hole 99. The through-hole 77 overlaps the discharge hole 99 when the first main surface of the circuit board 7 is viewed from the front side.

With this structure, the piezoelectric blower 28 sucks the gas from the suction hole 89 and discharges the gas from the discharge hole 99 when driven. The piezoelectric blower 8 discharges the gas discharged from the discharge hole 99 of the piezoelectric blower 28 from the discharge hole 99 to the outside of the inhalation device 701 via the through-hole 77 of the circuit board 7 and the exhaust cavity 47 when driven.

In the inhalation device 701, the gas discharged by the piezoelectric blower 8 passes through the through-hole 77 of the circuit board 7. Accordingly, in the inhalation device 701, the piezoelectric blowers 8 and 28 can be disposed near the circuit board 7 or on the circuit board 7.

That is, in the inhalation device 701, the circuit board 7 and the piezoelectric blowers 8 and 28 can be disposed so as to overlap. Accordingly, it is not necessary for the circuit board 7 and the piezoelectric blowers 8 and 28 to be arranged side by side in the longitudinal direction unlike the inhalation device 901 illustrated in FIG. 17.

Accordingly, the inhalation device 701 can have a smaller body size as in the case of the inhalation device 101.

In the inhalation device 701, two piezoelectric blowers, the piezoelectric blowers 8 and 28, are arranged in series. Accordingly, in the inhalation device 701, the maximum suction pressure can be increased to twice a suction pressure in the case where merely the piezoelectric blower 8 is arranged.

In the inhalation device 701, n=2, that is, the two piezoelectric blowers 8 and 28 are arranged in series. However, this is not a limitation. In operation, n≥3 may be acceptable, that is, three or more piezoelectric blowers may be arranged in series. In this case, the maximum discharge flow rate can be increased to n times.

The case where the n piezoelectric blowers are arranged in parallel will now be described.

Figure 16:
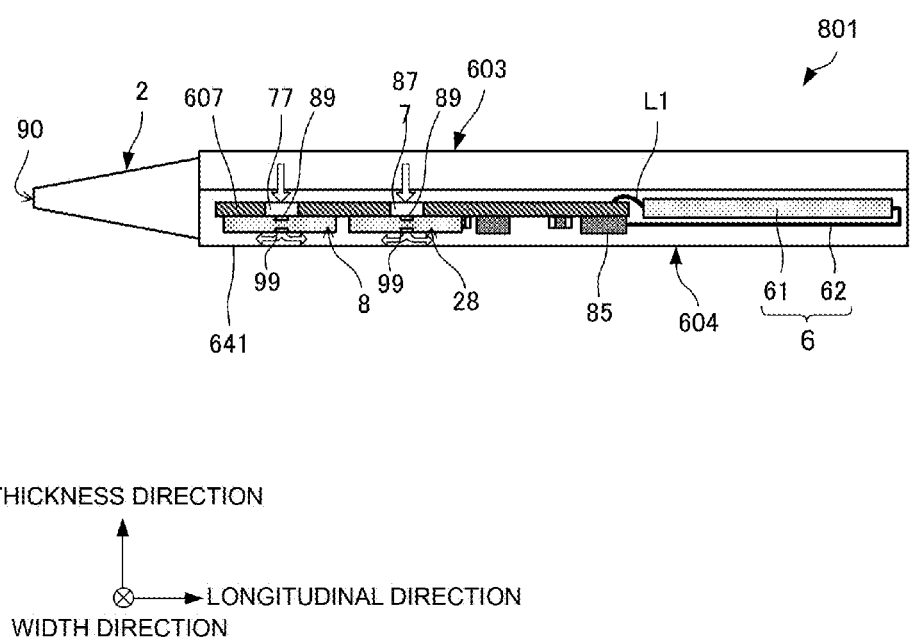
FIG. 16 is a sectional side view of an inhalation device 801 according to an eighth embodiment of the present disclosure.

FIG. 16 is a sectional side view of an inhalation device 801 according to an eighth embodiment of the present disclosure.

FIG. 16 illustrates the case of n=2. FIG. 16 is a schematic view in which a detailed illustration is omitted for simplification. Arrows in FIG. 16 represent the flow of a gas.

The inhalation device 801 according to the eighth embodiment differs from the inhalation device 601 in including a through-hole 877 and the piezoelectric blower 28, but including no protrusion 640. Other features are the same as in the inhalation device 601, and accordingly, the description thereof is omitted.

The structure of the piezoelectric blower 28 is the same as the piezoelectric blower 8. The piezoelectric blower 28 and the piezoelectric blower 8 are mounted on the same first main surface (one main surface) of the circuit board 607.

The circuit board 607 has the through-hole 877. The through-hole 877 of the circuit board 607 faces the suction hole 89. The through-hole 877 overlaps the suction hole 89 when the first main surface of the circuit board 607 is viewed from the front side. The electrode terminals 88 of the piezoelectric blower 28 are joined to the power-supply patterns of the circuit board 607.

The piezoelectric blower 8 is mounted on the first main surface (one main surface) of the circuit board 607. The through-hole 77 of the circuit board 607 faces the suction hole 89. The through-hole 77 overlaps the suction hole 89 when the first main surface of the circuit board 607 is viewed from the front side.

That is, the piezoelectric blower 8 and the piezoelectric blower 28 are arranged in parallel.

With this structure, the piezoelectric blower 28 sucks the gas from the suction hole 89 via the through-hole 877 and discharges the gas from the discharge hole 99 to the outside when driven. The piezoelectric blower 8 sucks the gas from the suction hole 89 via the through-hole 77 and discharges the gas from the discharge hole 99 to the outside when driven.

In the inhalation device 801, the gas to be sucked by the piezoelectric blower 8 and the gas to be sucked by the piezoelectric blower 28 pass through the through-holes 77 and 877 of the circuit board 607, respectively. Accordingly, in the inhalation device 801, the piezoelectric blowers 8 and 28 can be disposed near the circuit board 607 or on the circuit board 607.

That is, in the inhalation device 801, the circuit board 607 and the piezoelectric blowers 8 and 28 can be disposed so as to overlap. Accordingly, it is not necessary for the circuit board 607 and the piezoelectric blowers 8 and 28 to be arranged side by side in the longitudinal direction unlike the inhalation device 901 illustrated in FIG. 17.

Accordingly, the inhalation device 801 can have a smaller body size as in the case of the inhalation device 101.

In the inhalation device 801, two piezoelectric blowers, the piezoelectric blowers 8 and 28, are arranged in parallel. Accordingly, in the inhalation device 801, the maximum suction flow rate can be increased to twice a suction flow rate in the case where merely the piezoelectric blower 8 is arranged.

In the inhalation device 801, n=2, that is, the two piezoelectric blowers 8 and 28 are arranged in parallel, and the circuit board 607 has the two through-holes 77 and 877. However, this is not a limitation. In operation, n≥3 may be acceptable, that is, three or more piezoelectric blowers may be arranged in parallel, and the circuit board may have three or more through-holes (that is, the same number of the through-holes as the piezoelectric blowers). In this case, the maximum suction flow rate can be increased to n times.

In the embodiments, the shape of the nozzle 2 is not limited to the above examples and may be another shape. For example, in the case where the inhalation device 101 is used as a breast-milk inhalation device or a sputum inhalation device, the nozzle 2 may be formed in a funnel shape or a straw shape.

In the embodiments, the structure of the separator 3 that isolates the gas and the mixture (liquid) contained in the fluid may be another structure other than the structure described above. For example, the use of a valve structure in the separator 3 enables the gas and the liquid contained in the fluid to be readily isolated.

In the embodiments, the structure of the piezoelectric blower 8 may be another structure other than the structure described above. For example, the number of channels formed in the piezoelectric blower 8 on the discharge side, the number of channels on the inhale side, their routes, and other configurations may be appropriately changed.

Although air is used as a gas in the embodiments, the embodiments are not limited thereto. For example, a gas other than air may be used.

In the embodiments, the fluid to be inhaled is not limited to a liquid and may be a solid or a gelled material. The present disclosure can be applied to a dust collector that collects fine dust and particles, an apparatus that collects a paste and an adhesive that are excessively applied to a workpiece, and other apparatuses.

Finally, it should be understood that the embodiments are described by way of example in all their aspects, not by way of limitation. The scope of the present disclosure is not shown by the embodiments but by the scope of claims. The scope of the present disclosure includes all modifications having the same content and range as the scope of claims.

L1 . . . power line
L2 . . . power-supply line
2 . . . nozzle
3 . . . separator
4 . . . housing
6 . . . battery portion
7 . . . circuit board
8 . . . piezoelectric blower
10 . . . stationary portion
11 . . . cavity
28 . . . piezoelectric blower
31 . . . case
32 . . . tubular portion 33 . . . cap
34 . . . tubular portion
35 . . . recessed portion
36 . . . filter
41 . . . lower housing
42 . . . upper housing
43 . . . battery cover
47 . . . exhaust cavity
61 . . . battery
62 . . . battery case
71 . . . power switch
77 . . . through-hole
78 . . . power-supply pattern
81 . . . piezoelectric element
82 . . . structural body
83 . . . vibration plate
85 . . . electronic component
88 . . . electrode terminal
89 . . . suction hole
90 . . . inhalation cavity
91, 92, 93, 94, 95, 96, 97 . . . channel
98 . . . pump chamber
99 . . . discharge hole
100 . . . interior space
101 . . . inhalation device
201 . . . inhalation device
301 . . . inhalation device
303 . . . separator
304 . . . housing
401 . . . inhalation device
404 . . . housing
501 . . . inhalation device
504 . . . cover
505 . . . support
601 . . . inhalation device
603 . . . separator
604 . . . housing
607 . . . circuit board
640 . . . protrusion
641 . . . wall
701 . . . inhalation device
801 . . . inhalation device
877 . . . through-hole
901 . . . inhalation device
904 . . . housing
907 . . . circuit board

The invention claimed is:

1. An inhalation device comprising:
a piezoelectric blower having a suction hole for a gas, a discharge hole for the gas, and a piezoelectric element serving as a driving source; and
a circuit board having a through-hole facing the suction hole or the discharge hole and applying a drive voltage to the piezoelectric element to drive the piezoelectric blower,
wherein the through-hole overlaps the suction hole or the discharge hole facing the through-hole when a main surface of the circuit board is viewed from a front side.

2. The inhalation device according to claim 1,
wherein the piezoelectric blower includes a structural body, and
wherein the suction hole and the discharge hole are provided on a surface of the structural body.

3. The inhalation device according to claim 2,
wherein the suction hole opens in an upper surface of the structural body, and
wherein the discharge hole opens in a bottom surface of the structural body.

4. The inhalation device according to claim 2,
wherein a channel and a pump chamber are provided inside the structural body.

5. The inhalation device according to claim 4,
wherein a ceiling of the pump chamber includes a vibration plate enabling a flexural vibration, and the piezoelectric element is attached to the vibration plate.

6. The inhalation device according to claim 1,
wherein the piezoelectric blower is mounted on the main surface of the circuit board.

7. The inhalation device according to claim 6,
wherein a power-supply pattern for supplying the drive voltage is provided on the main surface of the circuit board, and
wherein the piezoelectric blower includes an electrode terminal joined to the power-supply pattern.

8. The inhalation device according to claim 1,
wherein the through-hole is wider than the suction hole or the discharge hole facing the through-hole and contains the suction hole or the discharge hole facing the through-hole when the main surface of the circuit board is viewed from the front side.

9. The inhalation device according to claim 1, further comprising:
a housing accommodating the piezoelectric blower and the circuit board,
wherein the housing has a first cavity exposed to an outside of the housing and in communication with the suction hole with a first channel interposed between the housing and the first cavity and a second cavity exposed to the outside of the housing and in communication with the discharge hole with a second channel interposed between the housing and the second cavity.

10. The inhalation device according to claim 9,
wherein the housing comprises a first housing having the first cavity and a second housing having the second cavity.

* * * * *